US006755793B2

(12) United States Patent
Lamoureux et al.

(10) Patent No.: US 6,755,793 B2
(45) Date of Patent: Jun. 29, 2004

(54) BONE MARROW EXTRACTION TOOL

(75) Inventors: Gary A. Lamoureux, Woodbury, CT (US); Milan J. Keklak, Thomaston, CT (US)

(73) Assignee: Worldwide Medical Technologies, Woodbury, CT (US)

( * ) Notice: Subject to any disclaimer, the term of this patent is extended or adjusted under 35 U.S.C. 154(b) by 332 days.

(21) Appl. No.: 09/927,702

(22) Filed: Aug. 1, 2001

(65) Prior Publication Data

US 2003/0153842 A1 Aug. 14, 2003

(51) Int. Cl.$^7$ .............................................. A61B 10/00
(52) U.S. Cl. ...................................................... 600/567
(58) Field of Search ................................ 600/564, 567; 606/167–185; 604/22

(56) References Cited

U.S. PATENT DOCUMENTS

| 4,785,826 A | | 9/1988 | Ward |
| 5,357,974 A | * | 10/1994 | Baldridge .................... 600/567 |
| 6,063,037 A | * | 5/2000 | Mittermeier et al. ........ 600/567 |

FOREIGN PATENT DOCUMENTS

| DE | 200 10 879 U | 10/2000 |
| EP | 0 852 127 | 7/1998 |
| WO | WO96/27330 | 9/1996 |

* cited by examiner

Primary Examiner—Max F. Hindenburg
Assistant Examiner—David J. McCrosky
(74) Attorney, Agent, or Firm—McCormick, Paulding & Huber LLP

(57) ABSTRACT

This bone marrow extraction tool comprises an outer cannula having an interiorly and exteriorly tapered marrow-receiving distal end, and an inner cannula slidably disposed in the outer cannula and having a distal end formed with diametrically opposed narrow and wide longitudinal slots to define resilient sectors. The wide slot is substantially longer than the narrow slot. The mouth of the inner cannula is adapted when forcibly engaging the interior taper of the outer cannula to diminish in diameter as the sectors are cammed inward and thereby compress marrow disposed in the mouth and squeeze it off from the marrow mass outside the outer cannula.

5 Claims, 2 Drawing Sheets

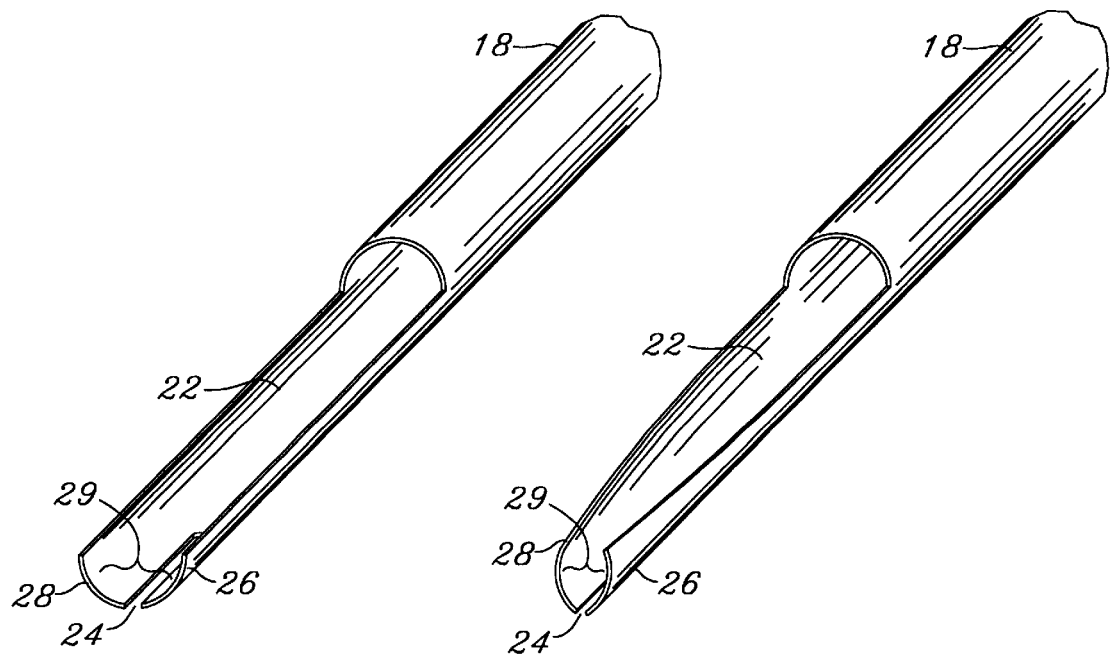
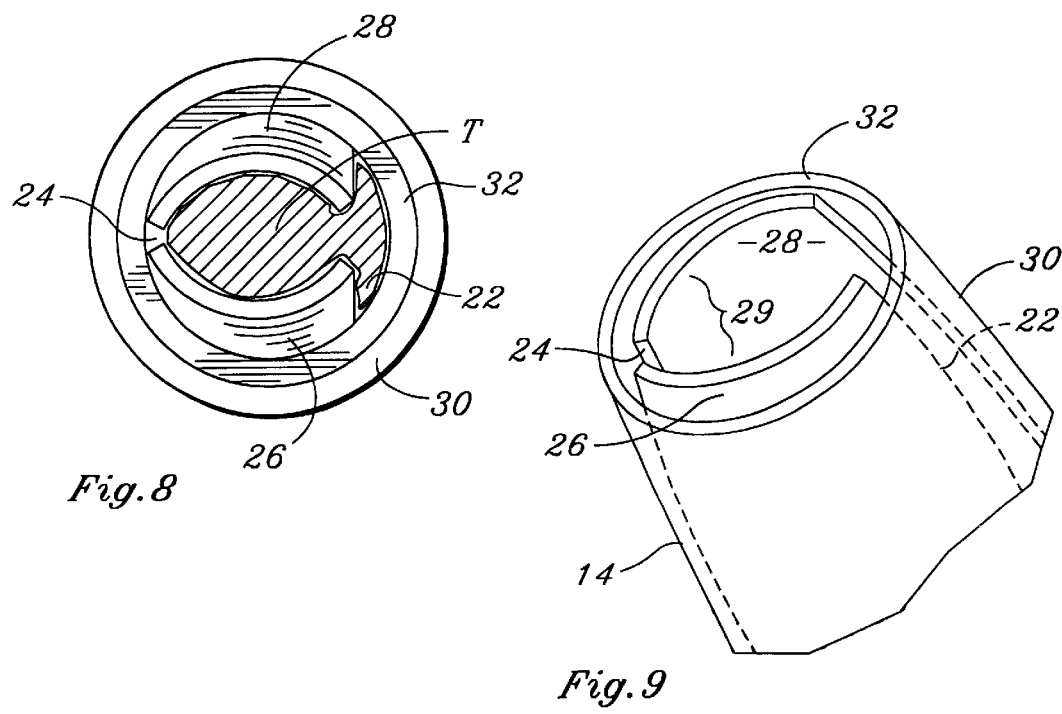

BONE MARROW EXTRACTION TOOL

FIELD OF THE INVENTION

This invention relates to a bone marrow extraction tool. More specifically, the invention relates to such a tool having means to separate the marrow sample from the marrow mass while the distal end of the tool is buried in the mass.

BACKGROUND OF THE INVENTION

There has been a need in bone marrow biopsy tools for improved means for severing the biopsy sample from the marrow mass. The prior art U.S. Pat. No. 5,807,277 to Swaim discloses relative rotation of inner and outer cannulas to cut off the sample, each cannula having a curving beveled nose. The present invention makes such relative rotation unnecessary.

SUMMARY OF THE INVENTION

The invention is a bone marrow extraction tool which comprises an outer cannula having an interiorly and exteriorly tapered marrow-receiving open distal end, and an inner cannula slidably disposed in the outer cannula and having a distal end formed with longitudinal slots. The slots define resilient sectors. The mouth of the inner cannula is adapted, when forcibly engaging the interior taper of the outer cannula to diminish in diameter as the sectors flex inward. The ends of the sectors compress marrow disposed in the mouth and squeeze it off from the marrow mass outside the outer cannula.

BRIEF DESCRIPTION OF THE DRAWINGS

Further objects and features of the invention will be clear to those skilled in the art from a review of the following specification and attached drawings, all of which present a non-limiting form of the invention. In the drawings:

FIG. 6 is a greatly enlarged perspective view of the lower end of the inner cannula in open position;

FIG. 7 is similar to FIG. 6 showing the lower end in closed position similar to the FIG. 4 condition;

FIG. 8 is a greatly enlarged end view comparable to FIG. 5 but showing the end of the severed biopsy material as it would appear when the tool is withdrawn after the biopsy procedure; and FIG. 9 is a greatly enlarged fragmentary perspective view of the distal end of the tool with the sectors closed.

DESCRIPTION OF THE PREFERRED EMBODIMENT

Figure 1:
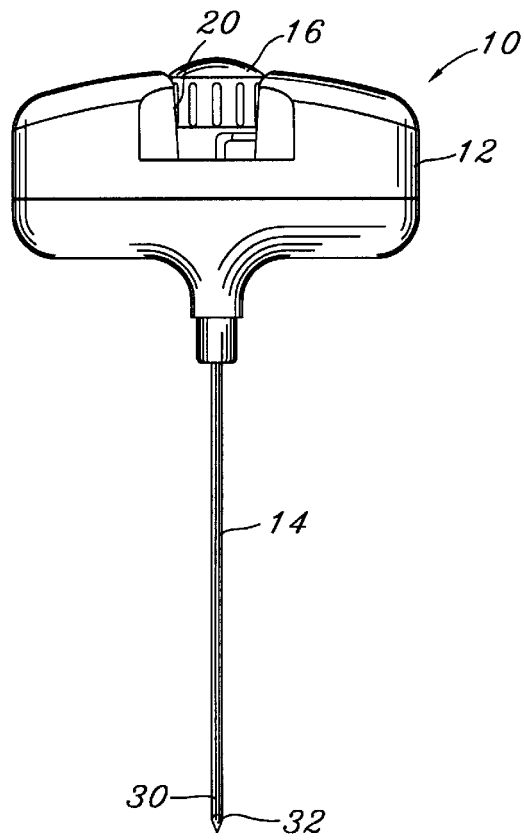
FIG. 1 is a front view of a biopsy tool known in the art.

A biopsy tool is, generally designated 10 in FIG. 1. It comprises a cross handle element 12 including an outer cannula 14 to provide a T-shaped structure. It also comprises a knob 16 in a recess 20 which mounts an inner stylet (not shown) locked in extended position inside the outer cannula for the cortex penetration step in a manner well-known in the art.

For the biopsy sampling under the present invention, the stylet is withdrawn up from the inside of the outer cannula, and an inner cannula 18 is telescoped into the outer cannula 14 with its upper end (not shown) extending up where the knob 16 is shown in FIG. 1.

Figures 2, 3:
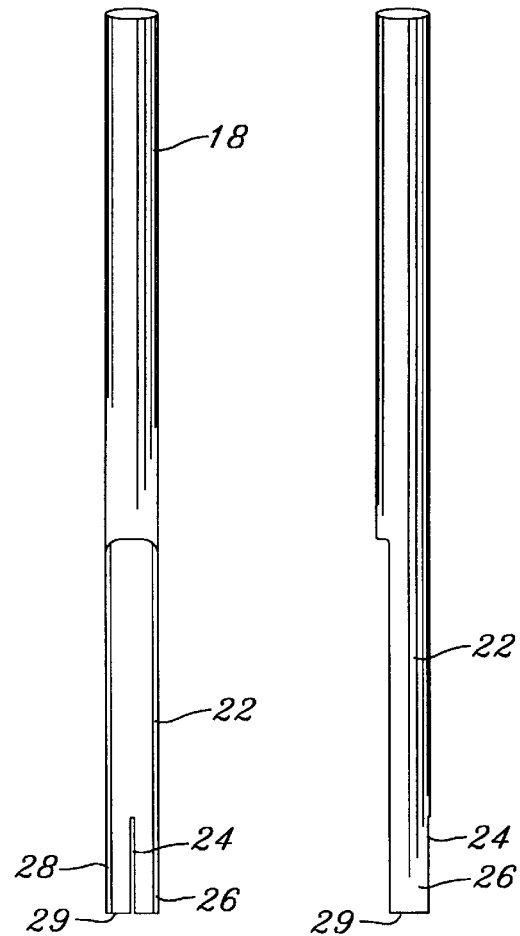
FIG. 2 is an enlarged fragmentary front view of the inner cannula embodying the invention useful with the tool of FIG. 1.
FIG. 3 is a side view of the inner cannula.
Figures 4, 5:
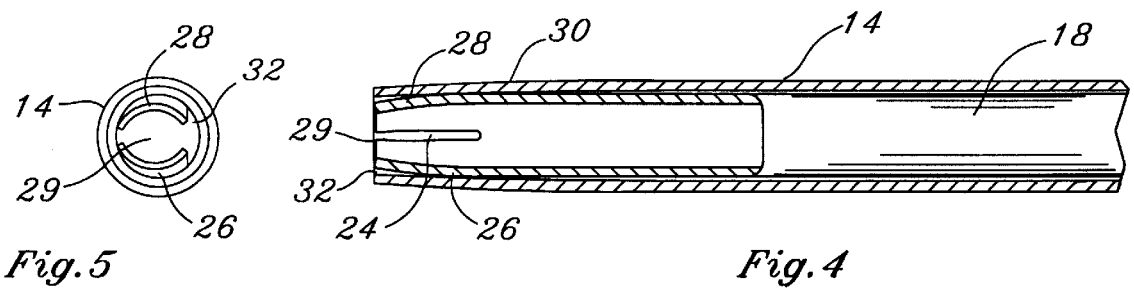
FIG. 4 is a slightly reduced fragmentary sectional view of the inner and outer assembly with the inner cannula pushed to its "home" or closed position for severing the biopsy sample.
FIG. 5 is an end view of the assembly of FIG. 4.

The inner cannula 18 (FIGS. 2, 3) is a stiff tube. A longitudinal portion of the distal end of the tube is formed with a wide slot 22 for access to extracted bone marrow and a thin slot 24 opposite the wide slot or notch 22. This defines arcuate relatively resilient end sectors 26, 28 terminating in a mouth 29. As shown in FIG. 4, the distal end of the outer cannula 14 is formed with a tapered end 30 tapered inside and outside, thinning as the open end 32 is approached.

When the outer cannula with the stylet in place has penetrated the cortex and the tapered end 30 is in the marrow mass, the inner cannula is substituted for the stylet and the upper or proximate end of the inner cannula 18 is pushed down into its recess 20. The resilient sectors of the inner cannula 18 are cammed inward as they forcibly engage the inside of the tapered end 30 as best seen in FIG. 4. This causes the two resilient sectors 26, 28 to move toward each other (FIG. 5) reducing the lower end of the notch 22 (FIG. 7) and also the lower end of the slot 24 diminishing the effective diameter of the mouth 29.

FIGS. 6, 7 and 8 in comparison demonstrate the closing of the sectors 26, 28 when the upper end of the inner cannula 18 is pushed all the way "home". The closing of the sectors 26, 28 (FIG. 9) toward each other narrows the mouth 29 and squeezes the captured tissue T (FIG. 8) at the distal end of the tool as shown in FIG. 8. The squeezing of the tissue separates the sample from the mass and retains the sample in the inner cannula when the tool is withdrawn. The inner cannula can be raised out of the outer cannula for access to the sample.

Variations in the invention are contemplated. While the invention has been disclosed in only one embodiment, it is not so limited but is of a scope defined by the following claim language which may be broadened by an extension of the right to exclude others from making, using or selling the invention as is appropriate under the doctrine of equivalents.

What is claimed is:

1. Improvement in a bone marrow extraction tool for removing marrow from a bone marrow mass comprising an outer cannula wherein the outer cannula is T-shaped being provided at its proximate end with a handle extending in opposite directions and formed with a central opening, said outer cannula having an interiorly tapered marrow-receiving distal end, and an inner cannula extending through said central opening and slidably disposed in the outer cannula, said inner cannula having a distal end formed with a plurality of longitudinal slots to define resilient sectors and a terminal marrow-receiving mouth, wherein said improvement comprises:

said inner cannula defining a narrow slot extending from a distal end at said terminal marrow-receiving mouth toward the proximate end of the inner cannula for a first distance and a wide slot extending from a distal end at said terminal marrow-receiving mouth toward the proximate end of the inner cannula for a second distance substantially greater than said first distance, said resilient sectors being so dimensioned and adapted to engage the interior taper of the outer cannula to cause said mouth to diminish in diameter as said resilient sectors are cammed inward when the inner cannula is slidably inserted into the outer cannula to thereby compress marrow disposed in the mouth of the inner cannula and squeeze it off from said bone marrow mass outside the outer cannula.

2. The improvement according to claim 1, wherein said outer cannula has an exteriorly tapered distal end.

3. The improvement according to claim 1, wherein said narrow slot is diametrically opposite said wide slot.

4. The improvement according to claim 1, wherein said second distance is on the order of four times said first distance.

5. The improvement according to claim 1, wherein said interiorly-tapered marrow-receiving distal end of the outer cannula is dimensioned with respect to the distal end of the inner cannula so as to cause the resilient sectors to substantially reduce the width of the wide slot at its distal end, whereby the diameter of the mouth is substantially reduced about marrow in the mouth of the inner cannula.

* * * * *